United States Patent
Mortier et al.

(10) Patent No.: US 11,331,149 B2
(45) Date of Patent: *May 17, 2022

(54) METHOD AND SYSTEM FOR DETERMINING A RISK OF HEMODYNAMIC COMPROMISE AFTER CARDIAC INTERVENTION

(71) Applicant: FEops NV, Ghent (BE)

(72) Inventors: Peter Eddy J. Mortier, Ingooigem (BE); Nic Debusschere, Ghent (BE); Gianluca De Santis, Ghent (BE); Tim DeZutter, Aalter (BE); Matthieu Robert Anna Firmin De Beule, Ghent (BE)

(73) Assignee: FEops NV, Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/361,156

(22) Filed: Jun. 28, 2021

(65) Prior Publication Data

US 2021/0322103 A1    Oct. 21, 2021

Related U.S. Application Data

(63) Continuation of application No. 17/003,653, filed on Aug. 26, 2020, now Pat. No. 11,051,885, which is a continuation of application No. 16/482,509, filed as application No. PCT/EP2018/052701 on Feb. 2, 2018, now Pat. No. 11,045,256, application No. 17/361,156, which is a continuation-in-part of application No. 14/399,781, filed as application No. PCT/EP2013/058392 on Apr. 23, 2013, now Pat. No. 10,789,772, said application No. 17/003,653 is a continuation-in-part of application No. 15/570,976, filed as application No. PCT/EP2016/059688 on Apr. 29, 2016, now Pat. No. 11,141,220.

(30) Foreign Application Priority Data

May 16, 2012  (WO) ................. PCT/EP2012/059207
Mar. 4, 2013  (WO) ................. PCT/EP2013/054276
May 1, 2015  (EP) ..................................... 15166130
Feb. 3, 2017  (EP) ..................................... 17154648

(51) Int. Cl.
| | |
|---|---|
| *A61B 34/10* | (2016.01) |
| *G16H 20/40* | (2018.01) |
| *G16H 50/50* | (2018.01) |
| *G16H 30/20* | (2018.01) |
| *A61B 5/021* | (2006.01) |
| *A61B 5/026* | (2006.01) |

(52) U.S. Cl.
CPC .............. *A61B 34/10* (2016.02); *A61B 5/021* (2013.01); *A61B 5/026* (2013.01); *G16H 20/40* (2018.01); *G16H 30/20* (2018.01); *G16H 50/50* (2018.01); *A61B 2034/102* (2016.02); *A61B 2034/105* (2016.02)

(58) Field of Classification Search
None
See application file for complete search history.

(56) References Cited

U.S. PATENT DOCUMENTS

| | | |
|---|---|---|
| 8,315,812 B2 | 11/2012 | Taylor |
| 8,548,778 B1 | 10/2013 | Hart et al. |
| 8,682,626 B2 | 3/2014 | Ionasec et al. |
| 10,275,876 B2 | 4/2019 | Reicher et al. |
| 10,789,772 B2 | 9/2020 | Mortier et al. |
| 11,045,256 B2 | 6/2021 | Mortier et al. |
| 11,051,885 B2 | 7/2021 | Mortier et al. |
| 11,069,136 B2 | 7/2021 | Mortier et al. |
| 2004/0225212 A1 | 11/2004 | Okerlund et al. |
| 2005/0043609 A1 | 2/2005 | Murphy et al. |
| 2007/0135707 A1 | 6/2007 | Redel et al. |
| 2008/0319448 A1 | 12/2008 | Lav et al. |
| 2009/0082660 A1 | 3/2009 | Rahn et al. |
| 2010/0042105 A1 | 2/2010 | Park et al. |
| 2011/0153286 A1 | 6/2011 | Zaeuner et al. |
| 2012/0053466 A1 | 3/2012 | Bianchi et al. |

(Continued)

FOREIGN PATENT DOCUMENTS

| | | |
|---|---|---|
| DE | 102012205504 A1 | 10/2013 |
| WO | WO-2013156546 A2 | 10/2013 |

(Continued)

OTHER PUBLICATIONS

Nucifora et al. (Circulation: Cardiovascular Imaging (2011) vol. 4, Issue 5:514-523).*
U.S Appl. No. 14/399,781 / U.S. Pat. No. 10,789,772, filed Nov. 7, 2014 / Sep. 29, 2020.
U.S Appl. No. 15/570,976, filed Oct. 31, 2017.
U.S Appl. No. 16/482,509 / U.S. Pat. No. 11,045,256, filed Jul. 31, 2019 / Jun. 29, 2021.
U.S Appl. No. 16/982,526, filed Sep. 18, 2020.
U.S Appl. No. 16/987,794, filed Aug. 7, 2020.
U.S Appl. No. 17/003,653 / U.S. Pat. No. 11,051,885, filed Aug. 26, 2020 / Jul. 6, 2021.

(Continued)

*Primary Examiner* — Lori A. Clow
(74) *Attorney, Agent, or Firm* — Eversheds Sutherland (US) LLP; Christopher C. Bolten; Nicola A. Pisano

(57) ABSTRACT

A method and system for predicting a measure of hemodynamic compromise as a result of transcatheter cardiac treatment. The method includes providing a patient-specific anatomical model representing cardiac region and an implant model representing a three-dimensional representation of a cardiac implant. The method includes virtually deploying said implant model into said patient-specific anatomical model. A deformation of the patient-specific anatomical model is calculated as a result of implant model deployment A measure of hemodynamic compromise is determined from the virtually deployed implant model and the deformed patient-specific anatomical model.

24 Claims, 4 Drawing Sheets

(56) References Cited

U.S. PATENT DOCUMENTS

| | | |
|---|---|---|
| 2014/0219537 A1 | 8/2014 | Carelsen et al. |
| 2015/0051884 A1 | 2/2015 | Grady et al. |
| 2015/0112659 A1 | 4/2015 | Mortier |
| 2015/0182255 A1 | 7/2015 | Shivkumar |
| 2015/0223773 A1 | 8/2015 | John et al. |
| 2015/0235569 A1 | 8/2015 | Babiker et al. |
| 2015/0370995 A1 | 12/2015 | Wakai |
| 2016/0038246 A1 | 2/2016 | Wang et al. |
| 2016/0166332 A1 | 6/2016 | Wang et al. |
| 2016/0199198 A1 | 7/2016 | Dietz et al. |
| 2016/0270859 A1 | 9/2016 | Park et al. |
| 2017/0000562 A1 | 1/2017 | Frank et al. |
| 2017/0150928 A1 | 6/2017 | Del Alamo De Pedro et al. |
| 2017/0270663 A1 | 9/2017 | Hoffmann et al. |
| 2017/0323481 A1 | 11/2017 | Tran et al. |
| 2017/0360510 A1 | 12/2017 | Bischoff et al. |
| 2018/0116725 A1 | 5/2018 | Ashikaga et al. |
| 2018/0289422 A1 | 10/2018 | Mortier et al. |
| 2018/0365838 A1 | 12/2018 | Lorenz et al. |
| 2019/0090951 A1 | 3/2019 | Camus et al. |
| 2019/0357981 A1 | 11/2019 | Mortier et al. |
| 2019/0392942 A1 | 12/2019 | Sorenson et al. |
| 2021/0022806 A1 | 1/2021 | De Beule et al. |

FOREIGN PATENT DOCUMENTS

| | | |
|---|---|---|
| WO | WO-2013171039 A1 | 11/2013 |
| WO | WO-2014009294 A1 | 1/2014 |
| WO | WO-2016038169 A1 | 3/2016 |
| WO | WO-2016177647 A1 | 11/2016 |
| WO | WO-2018141927 A1 | 8/2018 |
| WO | WO-2019179793 A1 | 9/2019 |
| WO | WO-2020182651 A1 | 9/2020 |

OTHER PUBLICATIONS

Antiga, et al., An Image-Based Modeling Framework for Patient-Specific Computational Hemodynamics, Medical & Biological Engineering & Computing, 46:1097-1112 (2008).

Auricchio, et al., Carotid Artery Stenting Simulation: From Patient-Specific Images to Finite Element Analysis, Medical Engineering and Physics, vol. 33:281-289 (2011).

Basri, et al., The Hemodynamic Effects of Paravalvular Leakage Using Fluid Structure Interaction; Transcatheter Aortic Valve Implantation Patient, Journal of Medical Imaging and Health Informatics, 6(5):1513-1518 (2016).

Capelli et al., "Patient-Specific Simulations of Transcatheter Aortic Valve Stent Implantation," Med. Medical & Biological Engineering & Computing, Jan. 29, 2012, 50:183-192 (2012).

De Santis, et al., Patient-Specific Computational Fluid Dynamics: Structured Mesh Generation from Coronary Angiography, Medical & Biological Engineering & Computing, vol. 48:371-380 (2010).

European Search Report dated Jul. 11, 2017 in EP Patent Appl. Serial No. 17154648.4.

European Search Report dated Oct. 2, 2018 in EP Patent Appl. Serial No. 18163655.6.

Extended EP Search Report dated Sep. 14, 2019 in EP Patent Appl. Serial No. 19161587.7.

Ghadimi, M.D., et al., Perioperative Conduction Disturbances After Transcatheter Aortic Valve Replacement, Journal of Cardiothoracic and Vascular Anesthesia, 27(6):1414-1420 (Dec. 2013).

Grbic, et al., Complete Valvular Heart Apparatus Model from 4D Cardiac CT, Field Programmable Logic and Application, vol. 6361:218-226 (2010).

International Search Report & Written Opinion dated Jun. 5, 2020 in Int'l PCT Patent Appl. Serial No. PCT/EP2020/056000.

International Search report and written opinion dated Jul. 15, 2016 in Int'l PCT Patent Application Serial No. PCT/EP2016/059688.

International Search report and written opinion dated Jul. 30, 2013 in Int'l PCT Patent Application Serial No. PCT/EP2013/058392.

International Search report and written opinion dated Jun. 4, 2018 in Int'l PCT Patent Application Serial No. PCT/EP2018/052701.

International Search report and written opinion dated May 31, 2019 in Int'l PCT Patent Application Serial No. PCT/EP2019/055907.

Lenoir, et al., Physics-Based Models for Catheter, Guidewire and Stent Simulation, Medicine Meets Virtual Reality, 14:305-310 (2006).

Morganti, et al., Simulation of Transcatheter Aortic Valve Implantation through Patient-Specific Finite Element Analysis: Two Clinical Cases, Journal of Biomechanics, 47:2547-2555 (2014).

Morlacchi, et al., Sequential Structural and Fluid Dynamic Numerical Simulations of a Stented Bifurcated Coronary Artery, Journal of Biomechanical Engineering, vol. 133, 11 pages (Dec. 2011).

Mortier, et al., A Novel Simulation Strategy for Stent Insertion and Deployment in Curved Coronary Bifurcations: Comparison of Three Drug-Eluting Stents, Annals of Biomedical Engineering, vol. 38(1):88-99 (Jan. 2010).

Rocatello et al., "Patient-Specific Computer Simulation to Elucidate the Role of Contact Pressure in the Development of New Conduction Abnormalities After Catheter-Based Implantation of a Self-Expanding Aortic Valve", Circulation Cardiovascular Interventions, pp. 1-9, (2018).

Russ, et al., Simulation of Transcatheter Aortic Valve Implantation Under Consideration of Leaflet Calcification, 35th Annual International Conference of the IEEE EMBS, Osaka, Japan, pp. 711-714 (Jul. 2013).

Schneider, et al., Modeling Mitral Valve Leaflets from Three-Dimensional Ultrasound, Field Programmable Logic and Application, vol. 6666:215-222 (2011).

Sirois, et al., Hemodynamic Impact of Transcatheter Aortic Valve Deployment Configuration, Journal of Medical Devices, 7(4):040922.1-040922.2 (Dec. 2013).

Steinberg, Cardiac Conduction System Disease After Transcatheter Aortic Valve Replacement, American Heart Journal, 164(5):664-671 (Nov. 2012).

Sun, et al., Simulated Elliptical Bioprosthetic Valve Deformation: Implications for Asymmetric Transcatheter Valve Deployment, Journal of Biomechanics, 43:3085-3090 (2010).

Viscardi, et al., Comparative Finite Element Model Analysis of Ascending Aortic Flow in Bicuspid and Tricuspid Aortic Valve, Artificial Organs, vol. 34:1114-1120 (2010).

Vy, et al., Review of Patient-Specific Simulations of Transcatheter Aortic Valve Implantation, HAL Archives, https:/hal-univ-rennes1.archives-ouvertes.fr/hal-01196296, pp. 1-33, (Sep. 9, 2015).

Wang et al., "Patient-specific modeling of biomechanical interaction in transcatheter aortic valve deployment," Journal of Biomechanics, vol. 45(11):1965-1971 (2012).

* cited by examiner

METHOD AND SYSTEM FOR DETERMINING A RISK OF HEMODYNAMIC COMPROMISE AFTER CARDIAC INTERVENTION

CROSS-REFERENCE TO RELATED APPLICATIONS

This application is a continuation of U.S. patent application Ser. No. 17/003,653, filed Aug. 26, 2020, now U.S. Pat. No. 11,051,885, which is a continuation of U.S. patent application Ser. No. 16/482,509, filed Jul. 31, 2019, now U.S. Pat. No. 11,045,256, which is a national phase application under 35 U.S.C. § 371 of PCT/EP2018/052701, filed Feb. 2, 2018, which claims priority to European Patent Application Serial No. 17154648.4, filed Feb. 3, 2017, and is also a continuation-in-part of U.S. patent application Ser. No. 14/399,781, filed Nov. 7, 2014, now U.S. Pat. No. 10,789,772, which is a national phase application under 35 U.S.C. § 371 of PCT/EP2013/058392, filed Apr. 23, 2013, which claims priority to PCT/EP2013/054276, filed Mar. 4, 2013, and PCT/EP2012/059207, filed May 16, 2012, the entire contents of each of which are incorporated herein by reference. This application is also a continuation-in-part of U.S. patent application Ser. No. 15/570,976, filed Oct. 31, 2017, which is a national phase application under 35 U.S.C. § 371 of PCT/EP2016/059688, filed Apr. 29, 2016, which claims priority to European Patent Application Serial No. 15166130.3, filed May 1, 2015, the entire contents of each of which are incorporated herein by reference.

FIELD OF THE INVENTION

The present invention relates to the field of pre-operative planning of transcatheter structural heart interventions, e.g. valve treatment, such as valve implantation and/or repair. More in particular, the invention relates to pre-operative prediction of the risk a patient developing hemodynamic compromise as a result of transcatheter valve treatment.

BACKGROUND TO THE INVENTION

The left ventricle of the heart pumps the blood to the aorta through the aortic valve. Aortic (valve) stenosis is a pathology occurring when the aortic valve does not open fully because the leaflets calcify, thicken and stiffen and, as a result, the blood flow going from the heart to the systemic circulation decreases. Aortic stenosis manifests itself in elderly people, with a prevalence going from 1.3% in over 65 and 4% in over 85 year old people. Currently it is one of the most common valvular heart diseases in the Western world and its prevalence is increasing with the aging population.

The traditional treatment for an aortic stenosis is the Surgical Aortic Valve Replacement (SAVR) aiming at reproducing the correct function of the native valve with an implanted valve. This invasive procedure requires total anesthesia, sternotomy (open-heart surgery) and cardiopulmonary bypass (the blood is pumped and oxygenated using an external machine), and is associated with about 6% in-hospital mortality for over 65 year old patients. Moreover, at least one-third of the patients with severe aortic stenosis are denied valve surgery as the risks associated with surgery are too high.

Trans-catheter aortic valve implantation (TAVI) or transcatheter aortic valve replacement (TAVR) is a minimally-invasive procedure for treating aortic stenosis: (1) the valve (e.g. a bioprosthetic valve made of porcine pericardium sutured on a metal stent) is crimped inside a catheter, (2) the catheter is inserted, for example, in the femoral artery, (3) pushed upstream along the aorta up to the aortic annulus and (4) the new valve is deployed within the diseased native valve. TAVI has the potential of treating high-risk patients and replacing the SAVR with a minimally-invasive intervention (no need for open-heart surgery or cardiopulmonary bypass) which can be performed in e.g. about 80 minutes. Main TAVI complications are vascular injury, stroke, cardiac injury (heart block, coronary obstruction, cardiac perforation), aortic regurgitation, cardiac conduction abnormalities and valve misplacement. Accurate pre operative planning is crucial to select the optimal device size and to anticipate potential difficulties.

Undersizing of a valve implant may lead to paravalvular aortic regurgitation, while oversizing may result in a rupture of the aortic annulus or in a suboptimal functional behavior of the implant (e.g. central regurgitation) or in conduction disturbances or in coronary obstruction. Currently available planning tools (Philips, Siemens, Pie Medical, Paeion) provide insights into the patient anatomy and can, for example, be used to determine the size of the aortic annulus, or to measure the distance between the valve plane and the coronary ostia. A problem with these tools is that they do not provide preoperative insights into the interaction between a certain implant device and the specific patient anatomy, and can thus not be used to predict complications such as regurgitation. Such insights are extremely valuable for interventional cardiologists.

Document US 2011/0153286 A1 discloses a method and system for virtual percutaneous valve implantation. In one embodiment of the application a patient-specific anatomical model of a heart valve is estimated based on 3D cardiac medical image data. An implant model representing a valve implant is virtually deployed into the patient-specific anatomical model of the heart valve. A library of implant models, each modeling geometrical properties of a corresponding valve implant, can be maintained. The implant models maintained in the library can be virtually deployed into the patient specific anatomical model of the heart valve to select one of the implant models for use in a percutaneous valve implantation procedure.

US 2011/0153286 A1 does not provide a prediction of the mechanical behavior and interaction of the patient-specific aortic root, ascending aorta and aortic valve leaflets with the deployment of a valve implant. Said document also does not account for calcification of aortic valve leaflets. Neither does it provide a means to study the hemodynamic performance of an implant deployed in the aortic valve. Balloon-expandable devices whose deployment is based on permanent plastic deformations of the metal cannot be modeled. There is a need for more precise valve sizing and positioning. Problem is that the aortic annulus is not circular, that the aortic annulus may deform and that calcium deposits may deform a valve frame. Another problem is that the aortic root visualized with Computed Tomography (CT) imaging changes in shape and size after TAVI. Also the geometry of the stent frame of the transcatheter aortic valve (TAV) is affected by the stiffness of the aortic root, by the presence of stiff calcified regions and by the exact device position.

Sub-optimal treatment planning can have two socioeconomic effects. On the one hand this gives higher costs for the health system. If the incorrect device/size of the TAV is chosen, the first TAVI procedure may fail and additional treatments, including a second TAVI procedure (valve-in-valve), SAVR, or rehospitalization may be necessary, with a considerable increase of the costs per patient. As a reference, one single TAVI procedure costs about 40 k Euro and the stented valve itself costs about 20 k Euro. On the other hand this leads to a lower prognosis. Sub-optimal treatment planning may result in peri-procedural complications, which affect both the life quality and the life expectancy of the patient. An oversized valve may rupture the annulus or dissect the aorta whereas an undersized valve may dislodge and migrate or can induce paravalvular regurgitation.

In WO2013/171039 A1 the present inventors described a solution to overcome at least part of the above-mentioned disadvantages. WO2013/171039 A1 provides an improved method for preoperative insights into the interaction of an implant device and specific patient anatomy, for better prediction of complications, such as regurgitation, for better prediction of the hemodynamic performance of an implant deployed in an aortic valve, and for better patient selection and stratification. Also WO2013/171039 A1 provides a web-based pre-operative planning service for TAVI using computer simulations that predict stent frame deformation and incomplete frame apposition, allowing to assess the risk of regurgitation and other complications such as coronary obstruction and conduction abnormalities prior to the intervention.

In WO2016/177647 A1 the present inventors described method for determining a measure of a risk of a patient developing cardiac conduction abnormalities and/or disorders, such as left bundle-branch block (LBBB), as a result of transcatheter structural heart intervention, such a transcatheter cardiac valve implantation/replacement or repair.

SUMMARY OF THE INVENTION

Transcatheter mitral valve replacement, TMVR, may lead to an obstruction of the left ventricular outflow tract, LVOT, so blood flow towards the aorta may be significantly reduced. TMVR may also lead to a compression/obstruction of the left circumflex coronary artery, LCX, and/or the coronary sinus. It has been found that LVOT obstruction after TMVR in patients with mitral annular calcification occurs in approximately 10% of the patients. TAVI may lead to an obstruction of the coronary arteries, due to the movement of the calcified native leaflets towards the coronary ostia, or due to the presence of the TAV itself. Coronary obstruction after TAVI occurs in 0.5-1% of cases.

Thus, transcatheter cardiac valve implantation/replacement or repair can lead to hemodynamic compromise. The hemodynamic compromise can be obstruction of a primary blood flow path in which the valve is implanted. Such obstruction can cause a drop (gradient) in blood pressure over the implanted device. The hemodynamic compromise can be obstruction of a secondary blood flow path in communication with the primary blood flow path, e.g. at the location of the implanted device. The hemodynamic compromise can be leakage (or regurgitation) with occurs in the primary blood flow path.

Hence, there is a need to predict hemodynamic compromise, such as obstruction and/or leakage, as a result of valve treatment. Hence, a physician can preoperatively predict whether, and to what extent, a procedure such as valve replacement will result in complications such as obstruction of an adjacent blood flow path, such as the LVOT, LCX, coronary sinus, or coronary artery.

According to an aspect is provided a method for predicting a measure of hemodynamic compromise as a result of transcatheter structural heart intervention, such a transcatheter cardiac valve treatment. The treatment may be transcatheter valve implantation/replacement or trans-catheter valve repair. The transcatheter cardiac valve may e.g. be a transcatheter aortic or mitral valve or tricuspid valve. The method includes providing an implant model representing a three-dimensional representation of a cardiac implant, such as a cardiac valve implant, e.g. an aortic valve implant or mitral valve implant. The implant model can represent a three-dimensional representation of a transcatheter mitral valve, TMV, or transcatheter aortic valve, TAV, or transcatheter tricuspid valve. The implant model can be a finite element representation of the cardiac implant. The method includes providing a patient-specific anatomical model representing a patient-specific cardiac region including a deployment site for the cardiac implant in a first blood flow path, such as a patient-specific cardiac valve region, and a second blood flow path, such as a LVOT or aorta. The patient-specific anatomical model may represent a patient-specific left ventricle and/or atrium and/or aorta or a part thereof. The patient-specific anatomical model can comprise a finite element mesh. The implant model is virtually, e.g. in silico, placed, e.g. deployed, into the patient-specific anatomical model at the deployment site. A deformation of the patient-specific anatomical model as a result of implant model deployment is calculated. From the virtually deployed implant model and the deformed patient-specific anatomical model, a measure of hemodynamic compromise in the deformed patient-specific anatomical model is determined. On the basis of the determined measure of hemodynamic compromise, a measure may be determined of the risk of the patient developing complications if an actual implant corresponding to the implant model were actually implanted in the anatomical region of the patient corresponding to the patient-specific anatomical model.

The method can be used for predicting obstruction of the second blood flow path. Then, from the virtually deployed implant model and the deformed patient-specific anatomical model, a measure of obstruction of the second blood flow path in the deformed patient-specific anatomical model is determined. On the basis of the determined measure of obstruction, a measure may be determined of the risk of the patient developing complications if an actual implant corresponding to the implant model were actually implanted in the anatomical region of the patient corresponding to the patient-specific anatomical model.

The method can be used for predicting obstruction of the first blood flow path. For example, it is possible that with the valve leaflets open an open area of the valve is reduced, e.g. due to a not well expanded or deployed valve. This can cause a pressure drop (or gradient) in the blood flow through the valve. Then, from the virtually deployed implant model and the deformed patient-specific anatomical model, a measure of obstruction of the first blood flow path in the deformed patient-specific anatomical model is determined. On the basis of the determined measure of obstruction, a measure may be determined of the risk of the patient developing complications if an actual implant corresponding to the implant model were actually implanted in the anatomical region of the patient corresponding to the patient-specific anatomical model.

The method can be used for predicting leakage in the first blood flow path. For example, it is possible that with the valve leaflets closed blood leaks around the outside of the implanted valve, between the valve and the surrounding tissue. Alternatively, or additionally, in the closed position the valve leaflets may not fully close, allowing blood to leak through the implanted valve. Then, from the virtually deployed implant model and the deformed patient-specific anatomical model, a measure of leakage in the first blood flow path in the deformed patient-specific anatomical model is determined. On the basis of the determined measure of leakage, a measure may be determined of the risk of the patient developing complications if an actual implant corresponding to the implant model were actually implanted in the anatomical region of the patient corresponding to the patient-specific anatomical model.

It will be appreciated that the method includes computer implemented steps. It will be appreciated that all above mentioned steps can be computer implemented steps.

A cardiac valve implant and a cardiac valve region of the patient is an important example of the present invention. Nevertheless, the invention can also be applied to other implants, such as stents. Although below is referred in particular to a cardiac valve implant and a cardiac valve region of the patient, it will be appreciated that the features and advantages also apply to other implants for the heart. Therefore, for the purpose of understanding the invention where herein is referred to a cardiac valve implant and cardiac valve region this similarly holds for other cardiac implants and/or other cardiac regions, including LAA, atrial or ventricular septal defect closure.

Optionally, the method includes providing the patient-specific anatomical model at a plurality of moments during the cardiac cycle, and determining the measure of hemodynamic compromise, at the plurality of moments. It will be appreciated that the geometry of the heart changes significantly during the cardiac cycle. Therefore, the measure of hemodynamic compromise may vary significantly during the cardiac cycle as well. Hence, determining the measure of hemodynamic compromise at a plurality of moments during the cardiac cycle allows to determine minimum and maximum values of the hemodynamic compromise.

Optionally, the measure of obstruction of the second blood flow path is a cross sectional area of the second blood flow path. The cross sectional area, for instance, e.g. substantially, orthogonal to the direction of blood flow has proven to be a reliable measure of obstruction. The cross sectional area of the second blood flow path after deployment of the implant model can be compared with a cross sectional area of the second blood flow path in the patient-specific anatomical model in which no implant model is deployed. This provides insight into the predicted change of cross sectional area available for blood flow after deployment of the implant. Also a volume reduction of a segment of the second blood flow path can be a good measure to quantify obstruction.

Optionally, the measure of obstruction of the second blood flow path is a ratio of a cross sectional area of the second blood flow path when the implant model is deployed divided by a cross sectional area of the second blood flow path in the patient-specific anatomical model in which no implant model is deployed. This takes into account deformation of the anatomy, e.g. a TMVR device pushing against the LVOT reducing LVOT area, and presence of the device, e.g. the remaining area is the deformed area minus area occupied by the device. The ratio provides insight into the predicted change of the cross sectional area due to implant deployment.

Optionally, the measure of obstruction of the first blood flow path is a cross sectional area of the first blood flow path, e.g. in view of valve leaflet positions. The cross sectional area, for instance, e.g. substantially, orthogonal to the direction of blood flow has proven to be a reliable measure of obstruction. The cross sectional area of the first blood flow path after deployment of the implant model can be compared with a cross sectional area of the first blood flow path in the patient-specific anatomical model in which no implant model is deployed. This provides insight into the predicted change of cross sectional area available for blood flow after deployment of the implant. Also a volume reduction of a segment of the first blood flow path can be a good measure to quantify obstruction.

Optionally, the measure of obstruction of the first blood flow path is a ratio of a cross sectional area of the first blood flow path when the implant model is deployed divided by a cross sectional area of the first blood flow path in the patient-specific anatomical model in which no implant model is deployed. The ratio provides insight into the predicted change of the cross sectional area due to implant deployment.

Optionally, the patient-specific anatomical model further includes fluid pressures in the cardiac region. Hence, deformation of the patient-specific anatomical model can be calculated taking into account the fluid pressure. It is also possible to use computational fluid dynamics, CFD. Hence, obstruction and/or leakage can be determined.

Optionally, the method includes the step of simulating a displacement of at least one valve leaflet of the cardiac valve implant. The measure of hemodynamic compromise, e.g. the measure of obstruction of the second blood flow path, can then be determined also on the basis of the leaflet displacement.

Optionally, the method includes the step of simulating a displacement of at least one valve native leaflet due to device-anatomy interaction and optionally hydrodynamic forces. The measure of hemodynamic compromise, e.g. the measure of obstruction of the second blood flow path, can then be determined also on the basis of the leaflet displacement.

Optionally, the displacement of the valve leaflet (of the implant and/or native valve) can be calculated using CFD, or fluid structure interactions, FSI. For example, the anterior mitral valve leaflet is displaced towards the LVOT by TMVR, but may further move during systole due to blood flow. This may be modelled as suggested.

Optionally, the measure of obstruction of the second blood flow path is a pressure gradient at the second blood flow path. Optionally, the measure of obstruction of the first blood flow path is a pressure gradient at the first blood flow path. Optionally, the measure of obstruction of the first blood flow path is a pressure gradient across the implant, e.g. the valve (i.e. non-zero pressure difference across the valve when valve is open).

Optionally, the measure of obstruction of the second blood flow path is a flow measure at the second blood flow path. Optionally, the flow measure is the maximum velocity at the second blood flow path or the extension of the cross sectional portion of the second blood flow path with velocity magnitude above a threshold. Optionally, the measure of obstruction of the first blood flow path is a flow measure at the first blood flow path. Optionally, the flow measure is the maximum velocity at the first blood flow path or the extension of the cross sectional portion of the first blood flow path with velocity magnitude above a threshold.

It will be appreciated that this method provides the advantage that the measure of the risk of the patient developing hemodynamic compromise, such as obstruction and/or leakage, as a result of transcatheter treatment of the cardiac valve can be predicted pre-operatively. Hence, it is possible to predict how likely e.g. a planned TAVI or TMVR procedure will result in hemodynamic problems.

Optionally, determining the measure of hemodynamic compromise includes determining an evolution of the hemodynamic compromise over time during the process of deployment. It is possible to determine the measure of hemodynamic compromise at a first moment and at a second moment. The first moment may be prior to the implant model being fully deployed into the patient-specific anatomical model. The second moment may be after the implant model has been fully deployed into the patient-specific anatomical model. It is also possible to determine the measure of the hemodynamic compromise at a plurality of first moments. Hence a time evolution of the hemodynamic compromise during deployment of the implant model can be determined. Optionally, time evolution of hemodynamic compromise after deployment is also determined. Hence, remodeling of the heart, due to the heart anatomy changing due to the prolonged presence of the implant, can be taken into account. For instance, hemodynamic compromise at one week, at one month, and at one year after treatment can be determined.

Optionally, determining the measure of hemodynamic compromise may include determining a series of situations of progressing deployment of the implant model into the patient-specific anatomical model. The situations may progressively differ by a predetermined amount or ratio of deployment. The deployment can include insertion of the implant model into the patient-specific anatomical model. The insertion can include travel of a model of a, collapsed, implant along a vessel. The series of situations can include situations of progressively differing positions of insertion up to an intended deployment position. The deployment can include expansion of the implant model in the patient-specific anatomical model. The series of situations can include situations of progressively differing stages of expansion of the implant model. For each of the situations of the series of situations the measure of hemodynamic compromise can be determined as described above. Hence, all stages of deployment can be modeled. The processing unit can be arranged to determine the situation of the series of situations in which the determined hemodynamic compromise is most significant, e.g. highest obstruction. The processing unit may be arranged to determine the measure of hemodynamic compromise in the situation of the series of situations in which the determined mechanical interaction is most significant for predicting hemodynamic problems, e.g. highest. The series of situations may be generated for a plurality of different deployment sites. The processing unit may be arranged to select the optimum deployment site.

It will be appreciated that the risk of the patient developing hemodynamic problems can be quantified by taking a combination of the determinations mentioned above.

Optionally, the method includes estimating the patient-specific anatomical model on the basis of a, preferably preoperative, cardiovascular 2D or 3D or 4D medical image data, such as a X-rays, CT-scan, an MRI image, echocardiography images or the like, and combinations thereof.

Optionally, the method includes estimating the patient-specific anatomical model on the basis of anatomical measurements, using for example, a parametric heart model.

Optionally, the implant model comprises a finite element mesh. Each element of said mesh can be featured by a set of nodes. Adjacent elements of said element can comprise mutually shared nodes with said element. Said element can be featured by material dependent parameters. Each element of said mesh can differ in material dependent parameters from an adjacent element of said element of said mesh.

Optionally, stiffness elements are provided to a plurality of nodes of a mesh of the anatomical model. A stiffness element induces a reacting force on the corresponding node of said mesh, wherein said force is dependent on the displacement of said node or on the distance between said node and a fixed position equal or very close to the initial position of said node.

Optionally, the step of virtually deploying the implant model into the patient-specific anatomical model includes a three-dimensional finite element analysis. Hence, deployment of the implant in the patient-specific anatomical model can be simulated in silico in three dimensions.

Optionally, the method includes virtually deploying the implant model into the patient-specific anatomical model at a plurality of different locations at and/or near the deployment site and determining the measure of obstruction of the second blood flow path for each of the different locations. Hence, it is possible to assess the risk of hemodynamic problems for the plurality of different locations of the implant. Hence, it is also possible to select the location for the implant associated with the lowest risk of developing hemodynamic obstruction problems. Such selected location can be used in pre-operative planning of a TAVI or TMVR procedure.

Optionally, the step of virtually deploying the implant model includes providing a plurality of implant models, each modeling geometrical and/or material properties of a corresponding implant; and virtually deploying each of the implant models into the patient specific anatomical model, and determining the measure of hemodynamic compromise for each of the implant models. Hence, it is possible to assess the risk of hemodynamic problems for each the plurality of different implant models. Hence, it is also possible to select the implant model associated with the lowest risk of developing hemodynamic obstruction problems. Such selected implant model can be used in pre-operative planning of a TAVI or TMVR or TTVR procedure. The method can include selecting a cardiac valve implant corresponding to one of the plurality of the implant models for a percutaneous implantation procedure. A cardiac valve implant associated with the selected implant model can be used in a percutaneous implantation procedure to minimize risk of the patient developing hemodynamic problems. It will be appreciated that it is also possible to virtually deploy each implant model of the plurality of implant models into the patient specific anatomical model at a plurality of different locations at and/or near the deployment site. Thus the implant models can be compared each at its optimal location.

Optionally, the method includes reporting the measure of hemodynamic compromise to a user. The measure of hemodynamic compromise, e.g. the measure of obstruction and/or leakage, may e.g. be displayed on a display, printed in hardcopy or the like. It is also possible to report an indication of the risk of the patient developing hemodynamic problems to the user.

According to an aspect is provided a system for determining, e.g. predicting, a measure of hemodynamic compromise as a result of transcatheter cardiac valve treatment. The system includes a processor. The processor is arranged for receiving an implant model representing a three-dimensional representation of a cardiac valve implant. The processor is arranged for receiving a patient-specific anatomical model representing a patient-specific cardiac region including a deployment site for the cardiac implant in a first blood flow path and a second blood flow path. The patient-specific anatomical model can comprise a finite element mesh. The processor is arranged for virtually deploying said implant model into said patient-specific anatomical model at the deployment site. The processor is arranged for calculating deformation of the patient-specific anatomical model as a result of implant model deployment. The processor is arranged for determining, from the virtually deployed implant model and the deformed patient-specific anatomical model, a measure of hemodynamic compromise in the deformed patient-specific anatomical model. The processor can be arranged for determining a measure of risk of the patient developing hemodynamic problems on the basis of the determined measure of hemodynamic compromise. Thus, the system can be used to perform the method as described above.

According to an aspect is provided a computer program product including computer implementable instructions. The computer program product can be stored on a non-transient data carrier. When implemented by a programmable computer the instructions cause the computer to retrieve an implant model representing a three-dimensional representation of a cardiac valve implant. When implemented by a programmable computer the instructions cause the computer to retrieve a patient-specific anatomical model representing a patient-specific cardiac region including a deployment site for the cardiac implant in a first blood flow path and a second blood flow path. The patient-specific anatomical model can comprise a finite element mesh. When implemented by a programmable computer the instructions cause the computer to virtually deploy said implant model into said patient-specific anatomical model at the deployment site. When implemented by a programmable computer the instructions cause the computer to calculate deformation of the patient-specific anatomical model as a result of implant model deployment. When implemented by a programmable computer the instructions cause the computer to determine, from the virtually deployed implant model and the deformed patient-specific anatomical model, a measure of hemodynamic compromise in the deformed patient-specific anatomical model. When implemented by a programmable computer the instructions can cause the computer to determine a measure of risk of the patient developing hemodynamic problems on the basis of the determined measure of hemodynamic compromise. Thus, the computer program product can be used to perform the method as described above.

It will be appreciated that all features and options mentioned in view of the method apply equally to the system and the computer program product. It will also be clear that any one or more of the above aspects, features and options can be combined.

BRIEF DESCRIPTION OF THE DRAWINGS

Embodiments of the present invention will now be described in detail with reference to the accompanying drawings in which.

DETAILED DESCRIPTION

Left ventricular outflow tract (LVOT) obstruction after a transcatheter mitral valve replacement (TMVR) procedure is a frequent complication. LVOT obstruction after TMVR in patients with mitral annular calcification may occur in approximately 10% of the patients. This can result in increased mortality after one year. Using the present technology, however, a predictor for the occurrence of LVOT obstruction or other hemodynamic compromise can be given.

Figure 1:
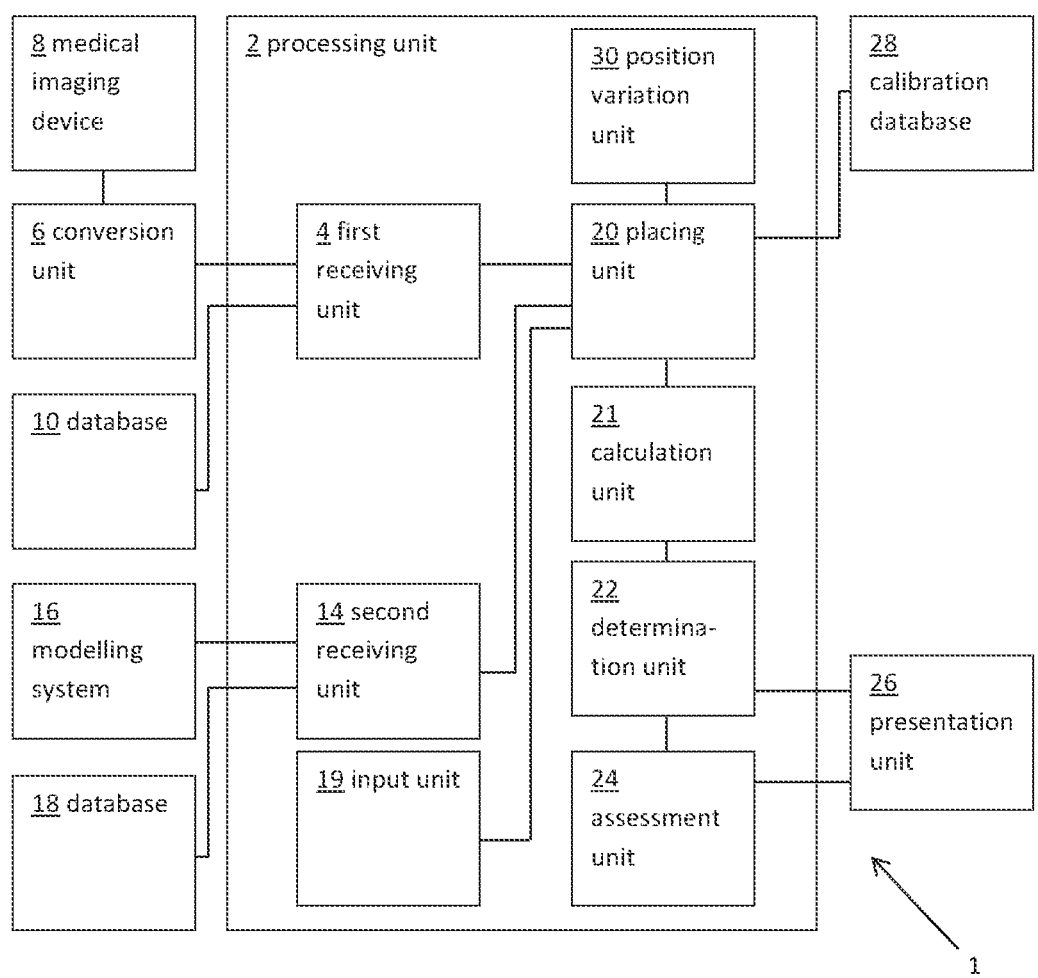
FIG. 1 is schematic representation of a system.

FIG. 1 shows a schematic example of a system 1 for predicting a measure of hemodynamic compromise, such as obstruction of a blood flow path, as a result of transcatheter cardiac valve treatment. The system includes a processing unit 2. The processing unit 2 includes a first receiving unit 4 for receiving a patient-specific anatomical model. Here the patient-specific anatomical model represents a patient-specific cardiac valve region.

In this example, the patient-specific anatomical model is provided as a three dimensional (3D) finite element model comprising a finite element mesh. In this example the patient-specific anatomical model is received from a conversion unit 6. The conversion unit 6 is arranged for receiving medical imaging data from a medical imaging device 8. The medical imaging data may be 2D, 2.5D (stacked 2D), 3D or 4D imaging data. The medical imaging data may be preoperative imaging data. The medical imaging device 8 may e.g. be a X-ray scanner, computer tomography (CT) device, an echocardiography device or a magnetic resonance imaging (MRI) device. In this example, the conversion unit 6 is arranged for creating the patient-specific 3D finite element model on the basis of the medical imaging data. Alternatively, or additionally, the patient-specific anatomical model can be received from a database 10.

The processing unit 2 further includes a second receiving unit 14 arranged for receiving an implant model representing a 3D representation of a cardiac valve implant, here a finite element representation. The 3D representation of the cardiac valve implant may e.g. be received from a 3D modelling system 16. Alternatively, or additionally, the 3D representation of the cardiac valve implant can be received from a database 18.

Figure 2:
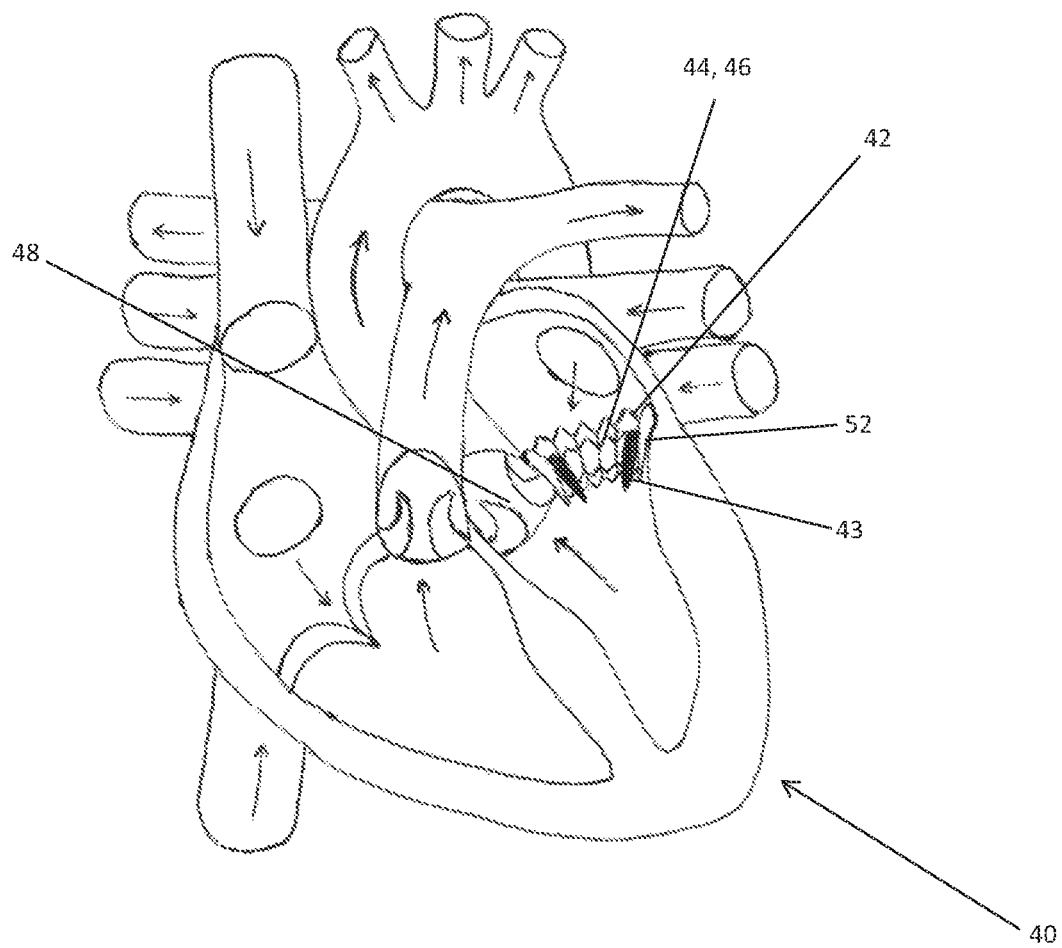
FIG. 2 is a schematic example in which an implant model and a patient-specific anatomical model are represented.

FIG. 2 shows a schematic example of a patient-specific anatomical model 40 of a cardiac valve region. FIG. 2 also shows a schematic example of an implant model 42. In this example the implant model 42 represents a mitral valve implant. The patient-specific anatomical model 40 includes a deployment site 44 for the cardiac implant 42 in a first blood flow path 46. The patient-specific anatomical model 40 also includes a second blood flow path 48. The first blood flow path 46 can e.g. be a blood flow path extending through the mitral valve, while the second blood flow path 48 is the LVOT. In another example, the first blood flow path can e.g. be a blood flow path extending through the aortic valve, while the second blood flow path is a coronary artery.

Returning to FIG. 1, the processing unit 2 includes a placing unit 20 arranged for virtually deploying said implant model into said patient-specific anatomical model. The placing unit can place the implant model 42 into the patient-specific anatomical model 40. The placing unit 20 can be arranged for bringing the implant model and the patient-specific anatomical model in a common model space. The processing unit 2 can be arranged for defining a deployment site 44 for the implant model in the first blood flow path 46 in the patient-specific anatomical model 40. The processing unit can include an input unit 19 arranged for receiving information relating to the deployment site 44. The input unit 19 can be associated with a graphical user interface arranged for allowing a user, such as a surgeon, to input a desired deployment site 44 for the implant model 42 in the patient-specific anatomical model 40. It is also possible that the processing unit 2 is arranged for autonomously determining, or proposing, the deployment site 44. The determined or proposed deployment site 44 can be based on a rule. The rule can be associated with a predefined location of an anatomical structure in the patient-specific anatomical model 40. The placing unit 20 can apply three dimensional finite element analysis.

The placing by the placing unit 20 also includes virtually expanding the implant model 42 into the patient-specific anatomical model 40. The expanded implant model 42 will abut against the patient-specific anatomical model 40. It will be appreciated that the patient-specific model 40 may deform, e.g. locally, due to the presence of the, e.g. expanded, implant model 42.

The processing unit 2 here includes a calculation unit 21 arranged for calculating a deformation of the patient-specific anatomical model 40 as a result of implant model 42 deployment. It will be appreciated that physical properties, such as stiffness, associated with both the implant model and the patient-specific anatomical model will determine the shape of the expanded implant model 42, the corresponding shape of the deformed patient-specific anatomical model 40, and a mechanical interaction between the implant model and the patient-specific anatomical model. The mechanical interaction can include one or more of force, pressure, stress, and strain between the implant model and the patient-specific anatomical model.

The processing unit 2 further includes a determination unit 22 arranged for determining, from the virtually deployed implant model 42 and the deformed patient-specific anatomical model 40, a predicted value of a measure of hemodynamic compromise. In this example, the determination unit 22 determines a predicted value of a measure of obstruction of the second blood flow path 48 in the deformed patient-specific anatomical model 40. In this example the determination unit 22 is arranged for determining a cross sectional area of the second blood flow path 48 after deployment of the implant model 42. Thereto the determination unit 22 can determine the deformation of the implant model 42 and the patient-specific anatomical model 40 due to deployment, and possible post-dilation. The deformations of both models 40, 42, in conjunction with modeled elasticities of the models 40, 42, allow to determine the force exerted by the one model onto the other. The elasticities of the models can be modeled as stiffnesses between nodes of the respective models.

Additionally, the determination unit 22 can be operated for determining a cross sectional area of the second blood flow path 48 before deployment of the implant model 42. Hence a difference in cross sectional area before and after deployment of the implant model 42 can be determined. The difference can be a measure for obstruction of the second blood flow path 48 due to presence of the implant model 42 and deformation of the patient-specific anatomical model 40. Alternatively, or additionally, the measure of obstruction of the second blood flow path 48 can be determined as a ratio of the cross sectional area of the second blood flow path 48 when the implant model 42 is deployed divided by the cross sectional area of the second blood flow path 48 in the patient-specific anatomical model 40 in which no implant model 42 is deployed.

In the above example, the determined hemodynamic compromise includes obstruction of the second blood flow path 48. Alternatively, or additionally, the determined hemodynamic compromise includes obstruction of the first blood flow path 46. It will be appreciated that the first blood flow path 46 may be somewhat obstructed by the presence of the implant. Thus, the calculation unit 21 can calculate a deformation of the patient-specific anatomical model 40 as a result of implant model 42 deployment. The determination unit 22 can be operated for determining a cross sectional area of the first blood flow path 46. This may e.g. be compared to a cross sectional area of the first blood flow path 46 before deployment of the implant model 42. Hence, the determination unit 22 can determine a measure of obstruction of the first blood flow path. It will be appreciated that possibly the way in which the implant is deployed in the first blood flow path 46 affects positioning of leaflets 43 of the implant model 42. Possibly the leaflets 43 do not fully open. Thereto, the determination unit 22 can calculate leaflet 43 position in the opened position. Thus, the determination unit 22 can take leaflet 43 positioning into account for determining an open area of the first blood flow path 46 for determining the measure of obstruction.

Alternatively, or additionally, the determination unit 22 can determine a pressure drop in the first blood flow path 46 along the implant model 42. The pressure drop is also representative for obstruction of the first blood flow path 46 due to the implant model 42.

Alternatively, or additionally, the determined hemodynamic compromise includes leakage of blood in the first blood flow path. For example, it is possible that with the implant valve leaflets 43 closed blood leaks around the outside of the implanted valve, between the valve and the surrounding tissue. Then, from the virtually deployed implant model 42 and the deformed patient-specific anatomical model 40, the determination unit 22 can determine a measure of leakage in the first blood flow path in the deformed patient-specific anatomical model. Thereto, the determination unit 22 can use calculated fluid pressures in the cardiac region. It is also possible to use computational fluid dynamics, CFD.

It is also possible that the implant valve leaflets 43 do not fully close due to the way in which the implant is deployed in the first blood flow path 46. This too may result in leakage of blood, in the closed position of the leaflets 43. Thereto, the determination unit 22 can calculate leaflet 43 position in the closed position. Thus, the determination unit 22 can calculate leakage.

The processing unit 2 can further include an assessment unit 24 arranged for determining a measure of risk of the patient developing hemodynamic problems, such as second blood flow path obstruction on the basis of the determined deformed models 40, 42. The determined risk can e.g. be expressed as a percentage, a number, a level or the like. The processing unit 2 is communicatively connectable to a presentation unit 26. The presentation unit 26 in this example is a display to display the measure of risk of the patient developing hemodynamic compromise to a user. It will be appreciated that the presentation unit can also present a representation, such as a numerical and/or graphical representation, of the obstruction to the user. Alternative, or additional, presentation units could be used, such as a hardcopy printer, an email server, a message service, a speaker device, etc.

It will be appreciated that the processing unit 2 may be arranged for applying a calibration. Thereto the processing unit 2 can include a calibration unit 28. Optionally, the predicted measure of hemodynamic compromise is determined for a plurality of patients. For each of these patients the predicted measure of hemodynamic compromise and the occurring or not-occurring of hemodynamic problems in reality are stored in a calibration database. From this calibration database a correlation between the predicted measure of hemodynamic compromise and the occurrence of hemodynamic problems in real life can be determined. From the correlation a measure of risk of the patient developing hemodynamic problems on the basis of the determined hemodynamic compromise can be determined. It will be appreciated that the calibration database can be updated over time.

Figure 3A:
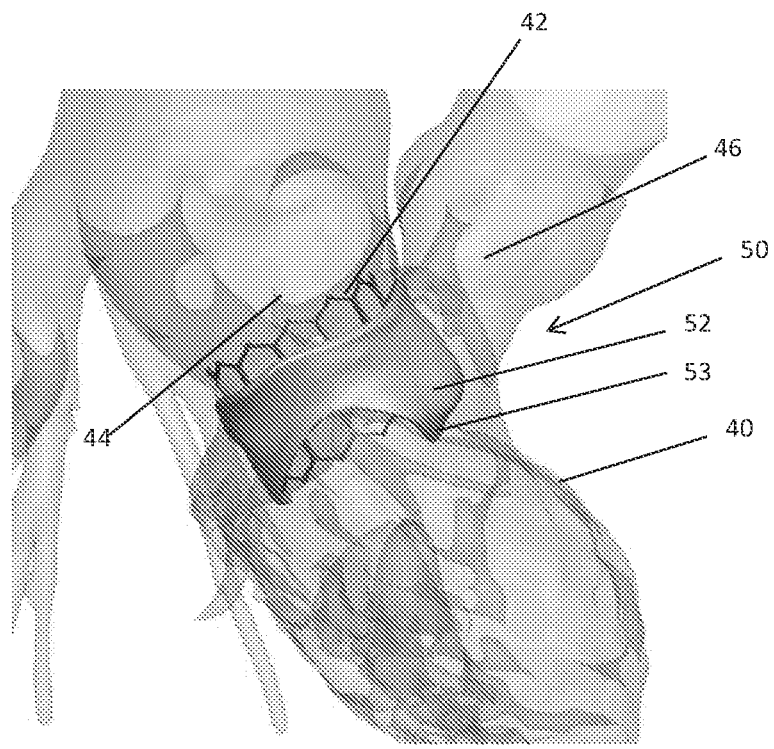
FIGS. 3a, 3b, 3c are an example wherein the implant model is deployed into the patient-specific anatomical model at a plurality of different locations.
Figure 3B:
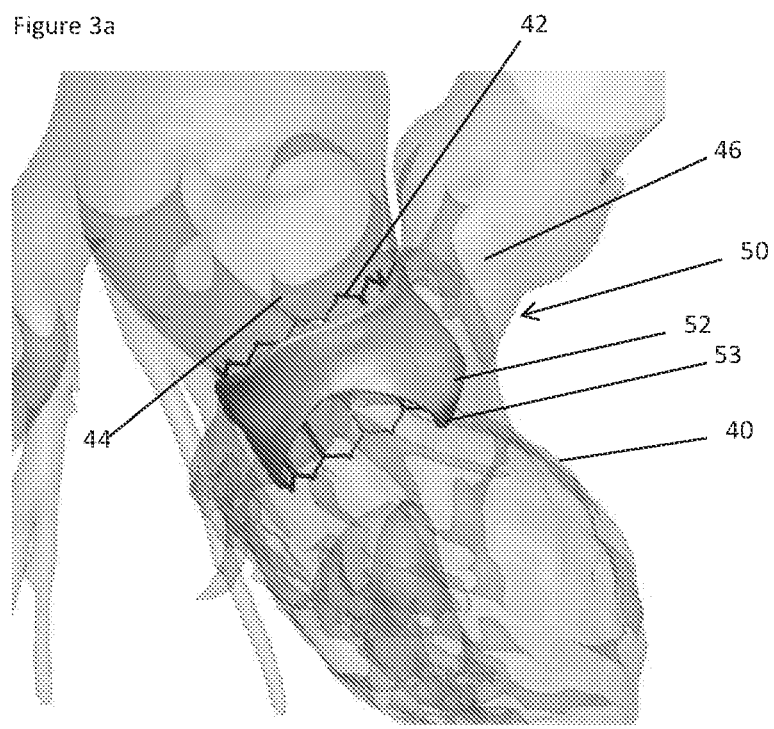
Figure 3C:
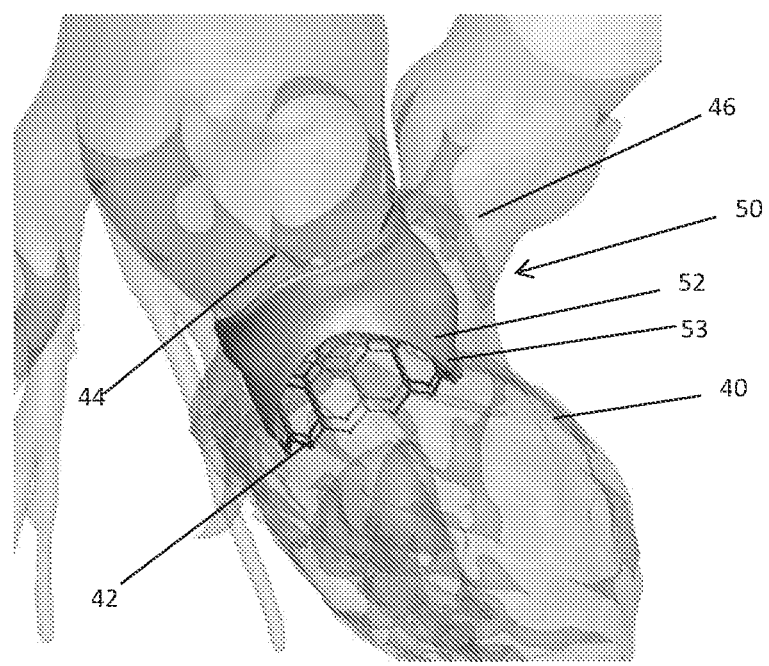

FIGS. 3a, 3b, 3c show an example wherein the implant model 42 is placed into the patient-specific anatomical model 40 at a plurality of different locations. In this example the patient-specific anatomical model 40 includes the region around the mitral valve 50. Here the first blood flow path 44 extends through the mitral valve 50. The second blood flow path 46 is formed by the LVOT and prolongs into the aorta. The native valve leaflets 52 can be identified in the FIGS. 3a-3c. In this example going from FIGS. 3a to 3b to 3c the implant model 42 is placed at three positions which are successively shifted by a few millimeters along the mitral valve. Thereto the processing unit 2 includes a position variation unit 30. As can be seen in the example of FIG. 3a, the tips 53 of the native valve leaflets 52 are freely overhanging the implant model 42. In 3c the native valve leaflets 52, including their tips 53, are pressed against the LVOT. Therefore, going from FIG. 3a to FIG. 3c the obstruction gradually increases. The assessment unit 24 determines the measure of obstruction for each of the different locations. From this analysis a user can learn which position of the implant provides the lowest risk of the patient developing hemodynamic problems. This information can be used in planning of the TMVR procedure. It is also possible that the processing unit 2 selects the position of the implant providing the lowest risk measure of hemodynamic problems. The processing unit can present the selected position as preferred the deployment site 44.

It will be appreciated that it is also possible that a plurality of different implant models 42 is provided. Each implant model 42 can represent geometrical and/or material properties of a corresponding real-life implant. The implant models 42 may e.g. differ in size, brand, construction, material or the like. Each of the implant models can then be placed into the patient specific anatomical model 40. The measure of hemodynamic compromise, and/or the risk of the patient developing hemodynamic problems, is then determined for each of the implant models 42. From this analysis it can be determined which one of the plurality of implant models has associated therewith the lowest measure of hemodynamic compromise and/or the lowest risk of the patient developing hemodynamic problems. A cardiac valve implant corresponding to the implant model 42 having the lowest associated measure of hemodynamic compromise and/or risk of the patient developing hemodynamic problems can then be selected for a real-life percutaneous implantation procedure. It will be appreciated that it is also possible that each of the implant models 42 is placed into the patient-specific anatomical model 40 at a plurality of different locations. Thus for each implant model a position of lowest hemodynamic compromise and/or risk can be determined. The lowest compromise and/or risk per implant model 42 can then be compared to select the cardiac valve implant for real-life percutaneous implantation.

It is also possible that the patient-specific model 40 includes time information. The patient-specific model may include a plurality of views, each corresponding to a different moment during the cardiac cycle. The measure of hemodynamic compromise for the implant model can be determined for each of the views. Hence, the measure of hemodynamic compromise can be determined at different moments during the cardiac cycle.

It will be appreciated that it is also possible that each of the implant models 42 is placed into the patient-specific anatomical model 40 at a plurality of different locations and analyzed for each of the views. Thus for each implant model a lowest measure of hemodynamic compromise and/or risk can be determined among the different locations and during the cardiac cycle. Also for each implant model a highest measure of hemodynamic compromise and/or risk can be determined among the different locations and during the cardiac cycle. The lowest and highest hemodynamic compromise and/or risk per implant model 42 can then be compared to select the cardiac valve implant for real-life percutaneous implantation. As can be seen in FIGS. 2 and 3a-3d, parts of the anatomy of the cardiac region may also contribute to the obstruction. For example the pressure of blood flowing through the first and/or second blood flow path can affect a position of parts of the anatomy, such as (calcified) native valve leaflets. According to an aspect, the calculation unit 21 calculates the deformation of the patient-specific anatomical model 40 as a result of implant model 42 deployment and fluid pressure. The interaction of the fluid and the structures of the patient-specific anatomical model can be included (fluid structure interaction, FSI) in the calculation of the deformed patient-specific anatomical model. Also computational fluid dynamics, CFD, can be used for determining the deformation of the patient-specific anatomical model 40 as a result of implant model 42 deployment and fluid mechanics inside the blood flow paths.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate embodiments, however, alternative embodiments having combinations of all or some of the features described in these separate embodiments are also envisaged.

It will be appreciated that in each of the examples, and in general, determining the measure of hemodynamic compromise may include determining a plurality of situations of progressing deployment of the implant model into the patient-specific anatomical model. The situations may progressively differ by a predetermined amount or ratio of deployment. The deployment can include insertion of the implant model into the patient-specific anatomical model. The insertion can include travel of a model of a, collapsed, implant along a vessel. The situations can include progressively differing positions of insertion up to the intended deployment position. The deployment can include expansion of the implant model in the patient-specific anatomical model. The situations can include progressively differing stages of expansion of the implant model. For each of the situations the measure of hemodynamic compromise can be determined as described above. Hence, all stages of deployment can be modeled. The processing unit may be arranged to determine the situation of the plurality of situations in which the determined hemodynamic compromise is least significant, e.g. lowest, or most significant, e.g. highest. The processing unit may be arranged to determine the measure of hemodynamic compromise in the situation of the plurality of situations in which the determined hemodynamic compromise is least or most significant for predicting hemodynamic problems.

It will be appreciated that such determining of a plurality of situations simulates determining an evolution of the measure of hemodynamic compromise between the implant model and the patient-specific anatomical model over time during the process of deployment.

It will be appreciated that simulating an evolution of the measure of hemodynamic compromise over time, may also be performed for a period of time after deployment, such as days, weeks, months, or even years after deployment. As such, remodeling of the heart, due to the heart anatomy changing due to the prolonged presence of the implant, can be taken into account.

In the examples, the implant model comprises a finite element model. It will be appreciated that it is also possible that the implant model comprises a mesh-free model. In the examples, the patient-specific anatomical model comprises a finite element model. It will be appreciated that it is also possible that the patient-specific anatomical model comprises a mesh-free model. It will be appreciated that the processing unit, first receiving unit, conversion unit, second receiving unit, input unit, modelling system, placing unit, calculation unit, determination unit, assessment unit, presentation unit, and/or position variation unit can be embodied as dedicated electronic circuits, possibly including software code portions. The processing unit, first receiving unit, conversion unit, second receiving unit, input unit, modelling system, placing unit, calculation unit, determination unit, assessment unit, presentation unit, and/or position variation unit can also be embodied as software code portions executed on, and e.g. stored in, a memory of, a programmable apparatus such as a computer, tablet or smartphone.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means, e.g. via the internet or cloud.

When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

However, other modifications, variations, and alternatives are also possible. The specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described.

In the claims, any reference sign placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A computer-implemented method of pre-operative planning for delivery of a left atrial appendage closure device in a patient's heart, the method comprising:
   obtaining a plurality of digital images of a patient's heart;
   obtaining a digital three-dimensional model of a left atrial appendage closure device;
   generating, from the plurality of digital images, and with a computer system, a patient-specific digital anatomical model of a patient's left atrium and left atrial appendage;
   determining, with the computer system, a pathway for delivering the left atrial appendage closure device into the patient-specific digital anatomical model of the patient's left atrium and left atrial appendage;
   virtually deploying, using the computer system, the digital three-dimensional model of the left atrial appendage closure device along the pathway and into the patient-specific digital anatomical model of the patient's left atrium and left atrial appendage;
   calculating, using the computer system, deformation of the digital three-dimensional model of the left atrial appendage closure device, in the deployed state, within the patient-specific digital anatomical model of the patient's left atrium and left atrial appendage; and
   determining, using the computer system, a measure of interaction between the digital three-dimensional model of the left atrial appendage closure device and the patient-specific digital anatomical model of the patient's left atrium and left atrial appendage.

2. The computer-based method of claim 1, wherein determining the measure of interaction comprises determining a blood flow path between the patient's left atrial appendage and the patient's left atrium in the digital anatomical model of the patient's left atrium and left atrial appendage.

3. The computer-based method of claim 2, wherein the measure of interaction is determined based on a cross-sectional area of the blood flow path.

4. The computer-based method of claim 1, wherein determining a measure of interaction further comprises determining, using the computer system, a measure of leakage in around a perimeter of the digital three-dimensional model of the left atrial appendage closure device.

5. The computer-based method of claim 1, further comprising providing the patient-specific digital anatomical model of the patient's left atrium and left atrial appendage at a plurality of moments during a cardiac cycle, and wherein the measure of interaction is determined at the plurality of moments.

6. The computer-based method of claim 1, further comprising determining the measure of interaction after simulating remodeling of the patient-specific digital anatomical model of the patient's left atrium and left atrial appendage caused by prolonged presence of the digital three-dimensional model of the left atrial appendage closure device.

7. The computer-based method of claim 1, wherein determining the measure of interaction comprises determining a degree of incomplete deployment of the digital three-dimensional model of the left atrial appendage closure device.

8. The computer-based method of claim 1, wherein the patient-specific digital anatomical model of the patient's left atrium and left atrial appendage further includes a fluid pressure in the patient-specific digital anatomical model of the patient's left atrium and left atrial appendage.

9. The computer-based method of claim 8, wherein determining the measure of interaction further includes determining a pressure gradient across the digital three-dimensional model of the left atrial appendage closure.

10. The computer-based method of claim 1, further comprising virtually deploying the digital three-dimensional model of the left atrial appendage closure device into the patient-specific digital anatomical model of the patient's left atrium and left atrial appendage at a plurality of different locations and determining the measure of interaction for each of the plurality of different locations.

11. The computer-based method of claim 1, wherein virtually deploying the digital three-dimensional model of the left atrial appendage closure device further comprises:
   providing a plurality of digital three-dimensional models of left atrial appendage closure devices having different geometrical or material properties; and
   virtually deploying each of the plurality of digital three-dimensional models of left atrial appendage closure devices into the patient specific digital anatomical model of the patient's left atrium and left atrial appendage, and
   determining the measure of interaction for each of the plurality of digital three-dimensional models of left atrial appendage closure devices.

12. The computer-based method of claim 11, further comprising determining a corresponding one of the plurality of digital three-dimensional models of left atrial appendage closure devices that causes a preferred degree of interaction as compared to others of the plurality of digital three-dimensional models of left atrial appendage closure devices.

13. The computer-based method of claim 1, further comprising displaying the measure of interaction on a computer system display.

14. A system for pre-operative planning for delivery of a left atrial appendage closure device in a patient's heart, the system comprising:
   a processor; and
   a memory for storing instructions to be executed by the processor, the instructions programmed to:
      receive a plurality of digital images of a patient's heart;
      receive a digital three-dimensional model of a left atrial appendage closure device;
      generate, from the plurality of digital images, a patient-specific digital anatomical model of a patient's left atrium and left atrial appendage;
      determine a pathway for delivering the left atrial appendage closure device into the patient-specific digital anatomical model of the patient's left atrium and left atrial appendage;
      virtually deploy the digital three-dimensional model of the left atrial appendage closure device along the pathway and into the patient-specific digital anatomical model of the patient's left atrium and left atrial appendage;
      calculate deformation of the digital three-dimensional model of the left atrial appendage closure device, in the deployed state, within the patient-specific digital anatomical model of the patient's left atrium and left atrial appendage; and
      determine a measure of interaction between the digital three-dimensional model of the left atrial appendage closure device and the patient-specific digital anatomical model of the patient's left atrium and left atrial appendage.

15. The system of claim 14, wherein, to determine the measure of interaction, comprises to determine a blood flow path between the the patient's left atrial appendage and the patient's left atrium in the digital anatomical model of the patient's left atrium and left atrial appendage.

16. The system of claim 15, wherein the instructions further are programmed to generate the patient-specific digital anatomical model of the patient's left atrium and left atrial appendage at a plurality of moments during a cardiac cycle, and to determine the measure of interaction at the plurality of moments.

17. The system of claim 16, wherein the instructions to determine the measure of interaction further comprise instructions programmed to determine a measure of leakage around a perimeter of the digital three-dimensional model of the left atrial appendage closure device.

18. The system of claim 14, wherein the instructions further comprise instructions programmed to determine the measure of interaction after simulating remodeling of the patient-specific digital anatomical model of the patient's left atrium and left atrial appendage caused by prolonged presence of the digital three-dimensional model of the left atrial appendage closure device.

19. The system of claim 14, wherein the instructions to determine the measure of interaction comprise instructions programmed to measure a degree of incomplete deployment of the digital three-dimensional model of the left atrial appendage closure device.

20. The system of claim 14, wherein the instructions further comprise instructions programmed to virtually deploy the digital three-dimensional model of the left atrial appendage closure device into the patient-specific digital anatomical model of the patient's left atrium and left atrial appendage at a plurality of different locations and to determine the measure of interaction for each of the plurality of different locations.

21. A non-transitory computer-readable medium storing computer implementable instructions that when executed by a programmable computer cause the computer to:
   receive a plurality of digital images of a patient's heart;
   receive a digital three-dimensional model of a left atrial appendage closure device;
   generate, from the plurality of digital images, a patient-specific digital anatomical model of a patient's left atrium and left atrial appendage;
   determine a pathway for delivering the left atrial appendage closure device into the patient-specific digital anatomical model of the patient's left atrium and left atrial appendage;
   virtually deploy the digital three-dimensional model of the left atrial appendage closure device along the pathway and into the patient-specific digital anatomical model of the patient's left atrium and left atrial appendage;
   calculate deformation of the digital three-dimensional model of the left atrial appendage closure device, in the deployed state, within the patient-specific digital anatomical model of the patient's left atrium and left atrial appendage; and
   determine a measure of interaction between the digital three-dimensional model of the left atrial appendage closure device and the patient-specific digital anatomical model of the patient's left atrium and left atrial appendage.

22. The non-transitory computer-readable medium of claim 21, wherein, to determine the measure of interaction, comprises to determine a blood flow path between the the patient's left atrial appendage and the patient's left atrium in the digital anatomical model of the patient's left atrium and left atrial appendage.

23. The non-transitory computer-readable medium of claim 21, wherein the instructions further are programmed to generate the patient-specific digital anatomical model at a plurality of moments during a cardiac cycle, and to determine the measure of interaction at the plurality of moments.

24. The non-transitory computer-readable medium of claim 21, wherein the instructions further are programmed to determine a measure of leakage around a perimeter of the digital three-dimensional model of the left atrial appendage closure device.

\* \* \* \* \*